(12) United States Patent
Mitchell

(10) Patent No.: US 10,512,268 B2
(45) Date of Patent: Dec. 24, 2019

(54) HERBICIDAL COMPOUNDS

(71) Applicant: Syngenta Participations AG, Basel (CH)

(72) Inventor: Glynn Mitchell, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/737,837

(22) PCT Filed: Jun. 28, 2016

(86) PCT No.: PCT/EP2016/065020
§ 371 (c)(1),
(2) Date: Dec. 19, 2017

(87) PCT Pub. No.: WO2017/001408
PCT Pub. Date: Jan. 5, 2017

(65) Prior Publication Data
US 2018/0295839 A1   Oct. 18, 2018

(30) Foreign Application Priority Data

Jul. 2, 2015   (GB) .................. 1511631.2

(51) Int. Cl.
*A01N 43/653*   (2006.01)
*C07D 403/12*   (2006.01)
*A01N 43/713*   (2006.01)

(52) U.S. Cl.
CPC ......... *A01N 43/653* (2013.01); *A01N 43/713* (2013.01); *C07D 403/12* (2013.01)

(58) Field of Classification Search
CPC ... C07D 403/12; A01N 43/653; A01N 43/713
See application file for complete search history.

(56) References Cited

FOREIGN PATENT DOCUMENTS

| EP | 2562174 A1 | 2/2013 |
| PK | 2105128424 A1 | 9/2015 |
| WO | 2009086041 A1 | 7/2009 |
| WO | 2013144234 A1 | 10/2013 |
| WO | 2014135654 A1 | 9/2014 |
| WO | 2014031971 A1 | 11/2014 |
| WO | 2014184074 A1 | 11/2014 |
| WO | 2015184074 A1 | 12/2015 |

OTHER PUBLICATIONS

International Search Report in International Applicaiton No. PCT/EP2016/065020 filed Jun. 28, 2016, dated Aug. 17, 2016.
Search Report under 17(5) in Application No. GB1511631.2 filed Jul. 2, 2015, dated Mar. 23, 2017.

*Primary Examiner* — John Pak
(74) *Attorney, Agent, or Firm* — BakerHostetler LLP; Toni-Junell Herbert

(57) ABSTRACT

The present invention relates to compounds of Formula (I) or an agronomically acceptable salt of said compounds wherein $A^1$, $A^2$, $R^1$, $R^2$, $R^3$ and $R^4$ are as defined herein. The invention further relates to herbicidal compositions which comprise a compound of Formula (I), and to their use for controlling weeds, in particular in crops of useful plants.

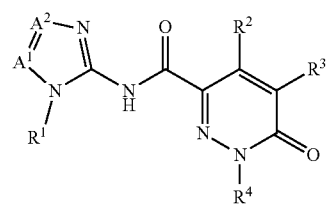

(I)

11 Claims, No Drawings

HERBICIDAL COMPOUNDS

RELATED APPLICATION INFORMATION

This application is a 371 of International Application No. PCT/EP2016/065020, filed Jun. 28, 2016, which claims priority to GB Application No. 1511631.2 filed Jul. 2, 2015, the contents of which are incorporated herein by reference herein.

The present invention relates to novel herbicidal compounds, to processes for their preparation, to herbicidal compositions which comprise the novel derivatives, and to their use for controlling weeds, in particular in crops of useful plants, or for inhibiting plant growth.

Herbicidal pyridazinones are disclosed in WO2014/031971. Herbicidal N-(tetrazol-5-yl)- and N-(triazol-5-yl)-arylcarboxamides are disclosed in, for example, WO 2013/139760. The present invention provides further improved herbicidal derivatives. Thus, according to the present invention there is provided a compound of Formula (I):

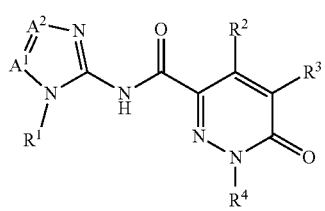

or an agronomically acceptable salt thereof,
wherein:—
$A^1$ and $A^2$ are independently selected from CH and N, wherein $A^1$ and $A^2$ are not both CH;
$R^1$ is selected from the group consisting of $C_1$-$C_6$alkyl-, $C_1$-$C_6$haloalkyl- and $C_1$-$C_6$alkoxy-$C_1$-$C_3$alkyl-;
$R^2$ is selected from the group consisting of $C_1$-$C_6$alkyl-, $C_1$-$C_6$haloalkyl-, halogen and —O—$R^5$;
$R^3$ is $C_3$-$C_8$cycloalkyl- which is optionally substituted by one or more substituents selected from the group consisting of halogen, $C_1$-$C_6$alkyl-, $C_1$-$C_6$alkoxy- and $C_1$-$C_6$haloalkyl-;
$R^4$ is selected from the group consisting of $C_1$-$C_6$alkyl-, $C_3$-$C_6$-cycloalkyl- and $C_1$-$C_6$ haloalkyl-; and
$R^5$ is selected from the group consisting of $C_1$-$C_6$alkyl-, $C_1$-$C_6$haloalkyl-, $C_1$-$C_6$alkoxy-$C_1$-$C_3$alkyl-.

$C_1$-$C_6$alkyl- includes, for example, methyl (Me, $CH_3$), ethyl (Et, $C_2H5$), n-propyl (n-Pr), isopropyl (i-Pr), n-butyl (n-Bu), isobutyl (i-Bu), sec-butyl and tert-butyl (t-Bu).

Cycloalkyl groups may be monocyclic alkyls such as cyclopropyl, cyclobutyl, cyclopentyl and cyclohexyl or bicyclic alkyls such as bicyclo[2.1.1]hexyl, bicyclo[2.2.1]heptyl and bicyclo[3.2.1]octyl. Where stated, the cycloalkyl may be optionally substituted by one or more substituents. The exact number of optional substituents will be dictated by the nature of the cycloalkyl group, but typically one, two or three substituents may exist.

Halogen (or halo) includes fluorine, chlorine, bromine or iodine. The same correspondingly applies to halogen in the context of other definitions, such as haloalkyl.

$C_1$-$C_6$haloalkyl- includes, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

$C_1$-$C_6$alkoxy- includes, for example, methoxy, ethoxy, propoxy, isopropoxy, n-butoxy, isobutoxy, sec-butoxy or tert-butoxy or a pentyloxy or hexyloxy isomer, preferably methoxy and ethoxy.

$C_1$-$C_6$alkoxy-$C_1$-$C_3$alkyl- includes, for example, methoxymethyl, methoxyethyl, ethoxymethyl, ethoxyethyl, n-propoxymethyl, n-propoxyethyl, isopropoxymethyl or isopropoxyethyl.

In one embodiment of the present invention is a compound of Formula (I) wherein $A^1$ is CH and $A^2$ is N. In another embodiment, $A^1$ is N and $A^2$ is CH. In a particularly preferred embodiment, both $A^1$ and $A^2$ are N.

In a preferred embodiment of the present invention, R' is selected from the group consisting of methyl, ethyl and n-propyl, methyl being especially preferred.

In another preferred embodiment, $R^2$ is selected from the group consisting of methyl, ethyl, chloro, trifluoromethyl. In a particularly preferred embodiment, $R^2$ is chloro.

In another preferred embodiment, $R^3$ is a $C_3$-$C_8$cycloalkyl- selected from the group consisting of cyclobutyl, cyclopentyl, cyclohexyl, bicyclo[2.1.1]hexane and bicyclo[2.2.1]heptane, wherein said $C_3$-$C_8$cycloalkyl- is optionally substituted by one or more (e.g 1, 2 or 3) substituents selected from the group consisting of halogen (preferably fluorine and/or chlorine), $C_1$-$C_6$alkyl- (preferably methyl and/or ethyl), $C_1$-$C_6$alkoxy- (preferably methoxy or ethoxy) and $C_1$-$C_6$haloalkyl- (preferably trifluoromethyl). In a particularly preferred embodiment, $R^3$ is cyclopentyl or cyclohexyl either of which may be optionally substituted by one or more (e.g 1, 2 or 3) substituents selected from the group consisting of halogen (preferably fluorine and/or chlorine), $C_1$-$C_6$alkyl- (preferably methyl and/or ethyl), $C_1$-$C_6$alkoxy- (preferably methoxy or ethoxy) and $C_1$-$C_6$haloalkyl- (preferably trifluoromethyl). In one particular embodiment, $R^3$ is cyclohexyl.

In another preferred embodiment, $R^4$ is selected from the group consisting of methyl, ethyl, and cyclopropyl. In a particularly preferred embodiment, $R^4$ is methyl.

Compounds of Formula I or II may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners.

Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, 16$^{th}$ Edition (BCPC), 2012. The reference to cloquintocet-mexyl also applies to a lithium, sodium, potassium, calcium, magnesium, aluminium, iron, ammonium, quaternary ammonium, sulfonium or phos-phonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area (escapes), or which grow from seed left over from a previous planting of a different crop (volunteers). Such volunteers or escapes may be tolerant to certain other herbicides.

The compounds of the present invention can be prepared according to the following schemes.

Scheme 1:- Reaction of an activated carboxylic acid with a 1-alkyl-5-aminotetrazole or an aminotriazole:

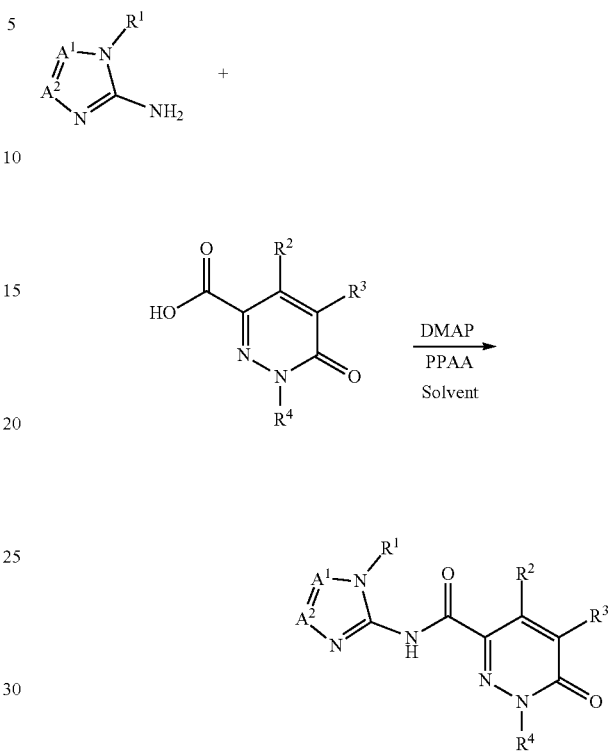

Scheme 2:- Reaction of an activated carboxylic acid with a 5-(alkylamino)tetrazole:

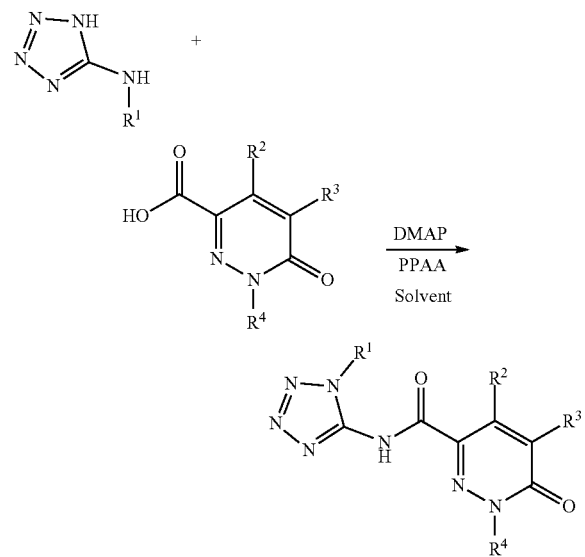

In each case, DMAP is 4-(dimethylamino) pyridine, PPAA is 1-propanephosphonic acid cyclic anhydride, the solvent is a non-protic organic solvent such as ethyl acetate, tetrahydofuran, 1,4-dioxane or dichloromethane, and the reaction may be subjected to heating by microwave irradiation.

Scheme 3: Reaction of an acid chloride with an aminotriazole or an aminotetrazole:

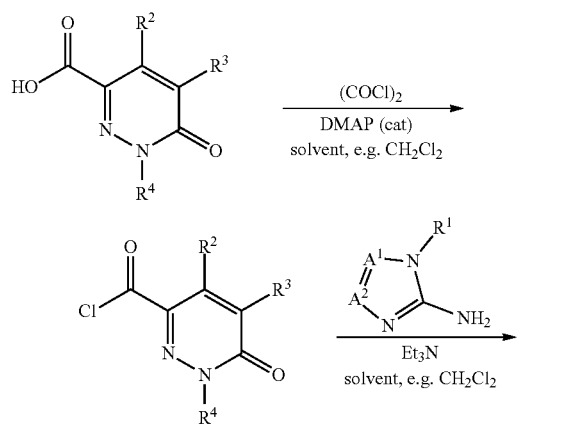

where THF is tetrahydrofuran and DBU is 1,8-diazabicyclo[5.4.0]undec-7-ene

Scheme 5: Reaction of a carboxylic ester with an aminotriazole or an aminotetrazole:

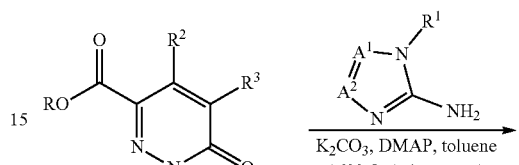

Scheme 4: Activation of an acid with N,N'-carbonyldiimidazole (CDI), and reaction with an aminotriazole or an aminotetrazole:

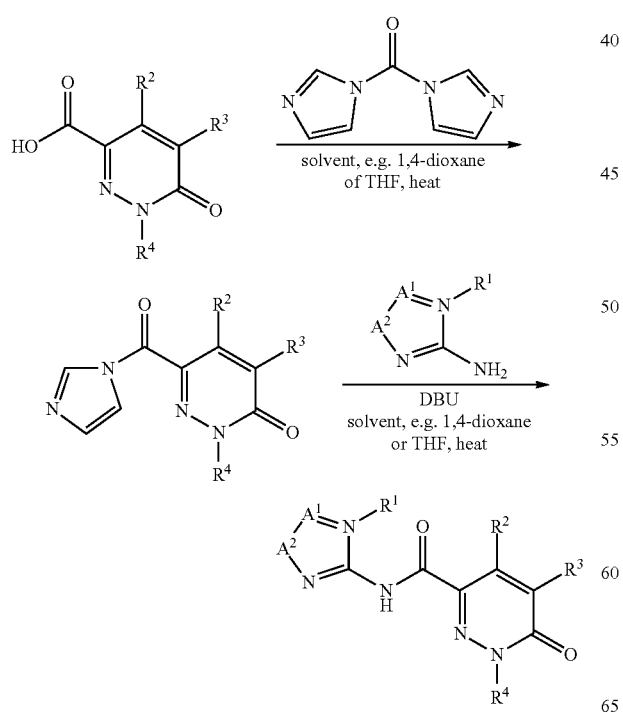

Scheme 6: Reaction of a chloropyridazinone with an alcohol:

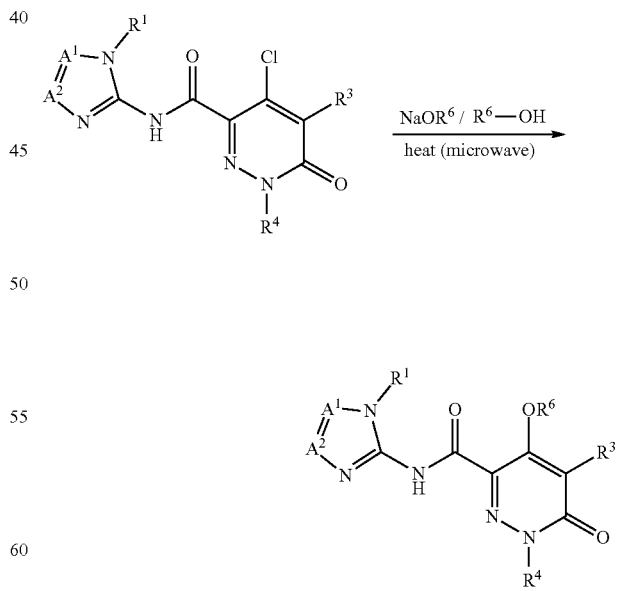

The carboxylic acids and esters are known, or can be prepared by known methods, or methods analogous to known methods. Examples of such methods are given in Schemes 7, 8 and 9, below.

Scheme 7.

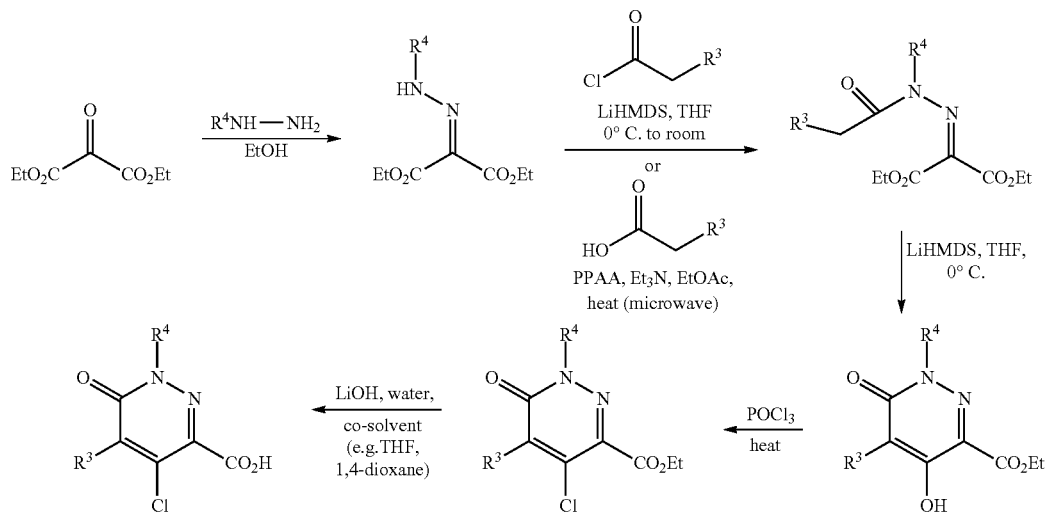

where THF is tetrahydrofuran, LiHMDS is lithium hexamethyl disilazide, PPAA is 1-propanephosphonic acid cyclic anhydride and EtOAc is ethyl acetate.

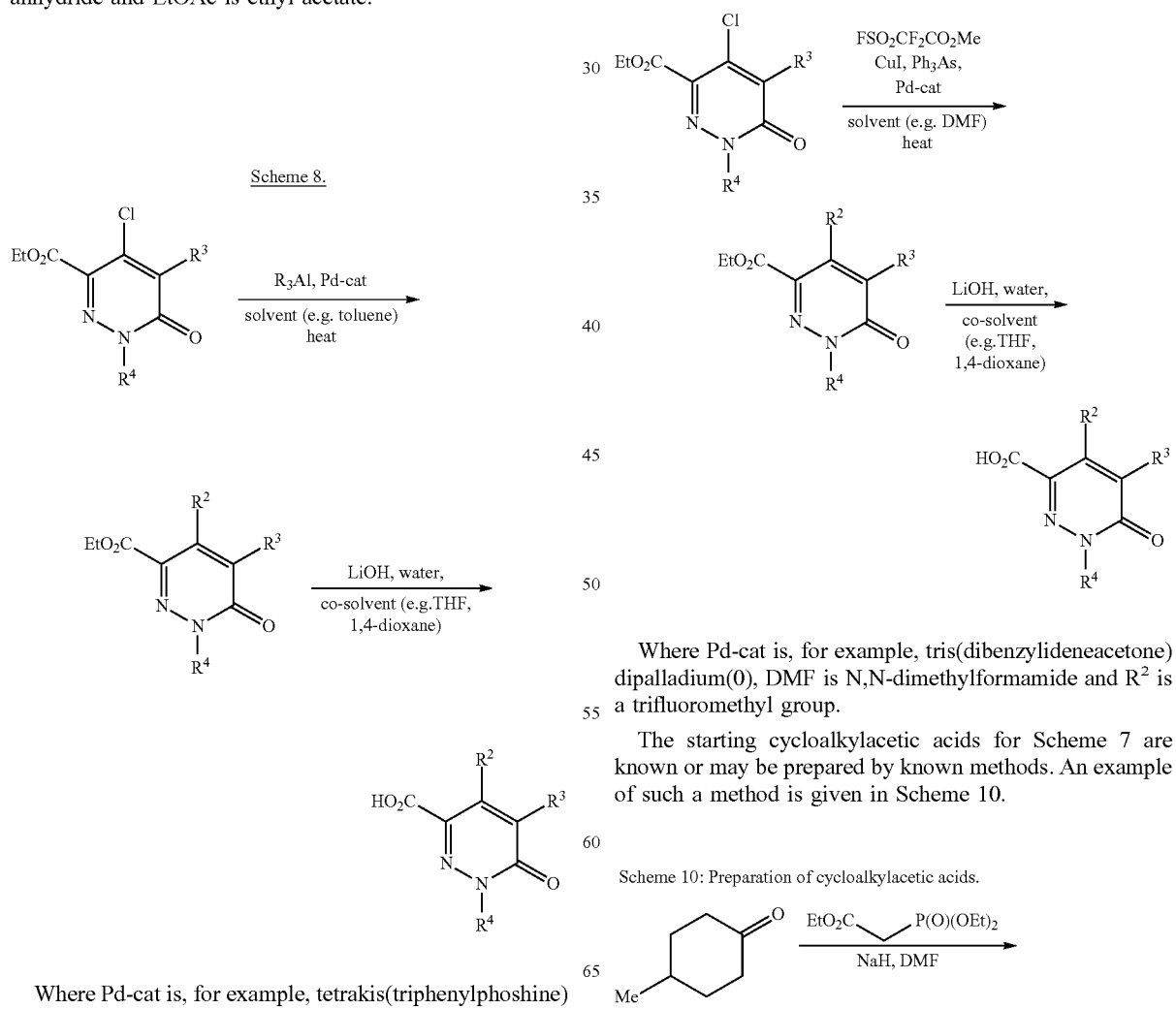

Where Pd-cat is, for example, tetrakis(triphenylphoshine) palladium(0) and $R^2$ is an alkyl group.

Where Pd-cat is, for example, tris(dibenzylideneacetone) dipalladium(0), DMF is N,N-dimethylformamide and $R^2$ is a trifluoromethyl group.

The starting cycloalkylacetic acids for Scheme 7 are known or may be prepared by known methods. An example of such a method is given in Scheme 10.

Scheme 10: Preparation of cycloalkylacetic acids.

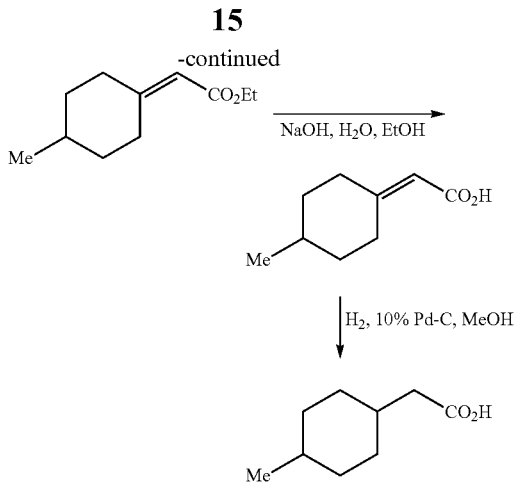

PREPARATIVE EXAMPLES

Example 1: Preparation of Compound 1.001

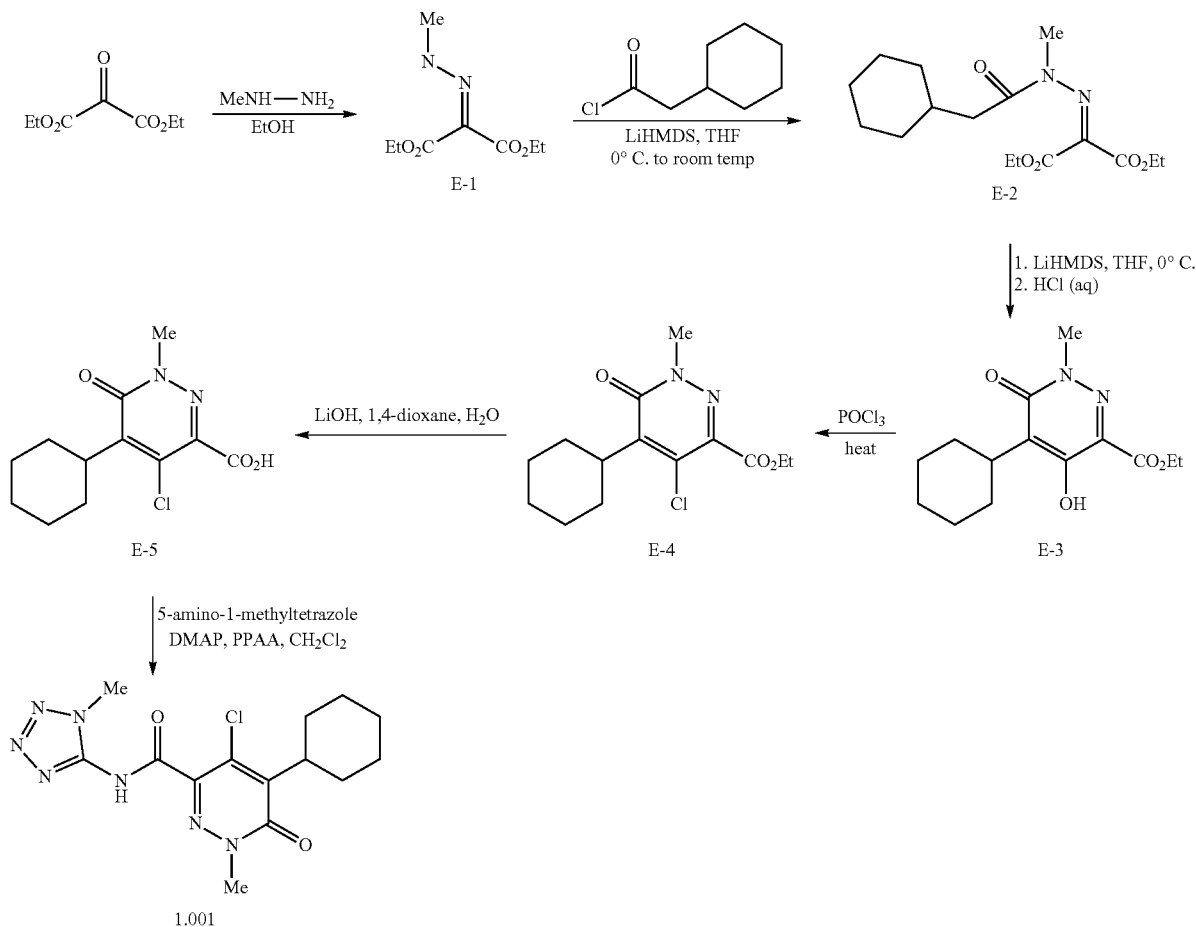

tion mixture was then slowly heated to 60° C. and stirred at that temperature for 6 hours. The mixture was then allowed to cool, and was stirred overnight at room temperature. The solvent was removed under reduced pressure, and the residue was diluted with ethyl acetate (ca. 500 mL). This was then washed with water (ca. 500 mL), and the aqueous washing was extracted with ethyl acetate (2×250 mL). The combined ethyl acetate layers were washed with brine (ca. 500 mL), dried over anhydrous sodium sulfate, and the solvent was removed under reduced pressure to leave the crude product as a thick orange gum. This was purified by column chromatography (100-200 mesh silica gel) using 10% ethyl acetate in hexanes as eluent to afford compound E-1 as a pale yellow oil (158.0 g).

1Hnmr (CDCl$_3$): δ 1.28-1.35 (m, 6H); 3.38-3.40 (d, 3H), 4.24-4.30 (m, 4H); 11.31 (br s, 1H)

Step 2:

A stirred solution of compound E-1 (0.50 g, 2.5 mmol) in tetrahydrofuran (10 mL) was cooled in an ice-bath under a nitrogen atmosphere and lithium hexamethyldisilazide (LiHMDS: 1M in THF; 2.8 mL) was added dropwise. The dark yellow solution was stirred, with cooling, for a further 30 mins, then 2-cyclohexylacetyl chloride (0.38 mL, 2.5 mmol) was added dropwise. When the addition was complete, the ice-bath was removed and the reaction mixture was stirred at room temperature for 30 minutes. The resultant mixture was poured into water, acidified with 2M HCl and extracted into ether (×2). The combined ether extracts were washed Step 1:

Methyl hydrazine (58.2 gm, 66.5 mL, 1.26 mol) was added dropwise to a stirred solution of diethyl ketomalonate (200.0 g, 1.15 mol) in ethanol (1.2 L) at room temperature (during the addition temperature rose to 45° C.). The reacwith brine, dried over anhydrous magnesium sulfate, then adsorbed on to silica-gel by evaporation under reduced pressure and dry-loaded onto a 40 g Rf cartridge. The mixture was then separated by chromatography (Combi-Flash Rf, eluting with an ethyl acetate/isohexane gradient) to afford compound E-2 (0.65 g) as a pale yellow oil.

1H NMR (CDCl$_3$) δ 4.39 (q, 2H), 4.32 (q, 2H), 3.33 (s, 3H), 2.72 (d, 2H), 1.93-1.78 (m, 1H), 1.76-1.61 (m, 5H), 1.38 (t, 3H), 1.34 (t, 3H), 1.30-1.10 (m, 3H), 1.07-0.96 (m, 2H)

Step 3:

A stirred solution of compound E-2 (540 mg, 1.654 mmol) in tetrahydrofuran (15 mL) was cooled to 0° C. in an ice-bath under a nitrogen atmosphere, and lithium hexamethyldisilazide (LiHMDS: 1M in THF; 2.0 mL) was added dropwise. The reaction mixture was stirred, with cooling, for a further 90 minute, when a precipitate had formed. The reaction mixture was quenched with saturated aqueous ammonium chloride solution, and the mixture was extracted with dichloromethane (×2). The combined dichloromethane extracts were washed with brine, dried by passing through a phase-separating cartridge, then adsorbed on to silica-gel by evaporation under reduced pressure and dry-loaded onto a 40 g GOLD Rf cartridge. The mixture was then separated by chromatography (CombiFlash Rf, eluting with an ethyl acetate/isohexane gradient) to afford compound E-3 (140 mg) as a white solid. 1H NMR (CDCl$_3$) δ 10.58 (br s, 1H), 4.49 (q, 2H), 3.83 (s, 3H), 3.10 (tt, 1H), 2.15-2.01 (m, 2H), 1.84-1.76 (m, 2H), 1.70 (d, 1H), 1.58-1.51 (m, 2H), 1.45 (t, 3H), 1.39-1.26 (m, 3H)

Step 4:

A stirred suspension of compound E-3 (275 mg, 0.9811 mmol) in phosphorus oxychloride (3 mL, 31.86 mmol) was heated to 60° C. for 1 hr, then heated to 80-85° C. for a further 90 minutes. The cooled reaction mixture was then added dropwise to water at room temperature, with stirring. The resultant mixture was cooled by the addition of ice, and extracted with ether (×2). The combined ether extracts were washed with brine, dried over anhydrous magnesium sulfate, then adsorbed on to silica-gel by evaporation under reduced pressure and dry-loaded onto a 24 g Rf cartridge. The mixture was then separated by chromatography (Combi-Flash Rf, eluting with an ethyl acetate/isohexane gradient) to afford compound E-4 (140 mg) as a white solid.

1H NMR (CDCl$_3$) δ 4.43 (q, 2H), 3.76 (s, 3H), 3.31-3.12 (m, 1H), 2.29-2.12 (m, 2H), 1.83 (dd, 2H), 1.72 (d, 1H), 1.53 (d, 2H), 1.41 (t, 3H), 1.38-1.26 (m, 3H)

Step 5:

A stirred solution of compound E-4 (245 mg, 0.820 mmol in 1,4-dioxane (8 mL) was treated dropwise with a solution of lithium hydroxide monohydrate (70 mg, 1.6 mmol) in water (2 mL), and the initially cloudy reaction mixture was stirred at room temperature for 2 hours. The mixture was evaporated under reduced pressure to leave a sticky cream solid, which was re-dissolved in dilute aqueous sodium hydroxide solution. This aqueous solution was extracted with ether (×2), and the ether extracts were discarded. The basic aqueous solution was then carefully acidified with 2M hydrochloric acid, resulting in the formation of a white precipitate. The suspension was extracted twice with dichloromethane, the combined dichloromethane extracts were dried by passing through a phase-separating cartridge, and evaporated under reduced pressure to afford pure compound E-5 as a white solid (205 mg). 1H NMR (CDCl$_3$/CD$_3$OD) δ=3.77 (s, 3H), 3.25 (t, 1H), 2.29-2.12 (m, 2H), 1.83 (m, 2H), 1.74 (m, 1H), 1.54 (d, 2H), 1.43-1.28 (m, 3H)

Step 6:

A stirred suspension of compound E-5 (100 mg, 0.369 mmol) in dry dichloromethane (8 mL) was treated with 5-amino-1-methyltetrazole (60 mg, 0.605 mmol) and 4-(dimethylamino)pyridine (DMAP: 90 mg, 0.737 mmol) in a 20 mL microwave tube, and the cloudy mixture was stirred at room temperature for 1 hour. A solution of 1-propanephosphonic acid cyclic anhydride (PPAA) in ethyl actetate (50 mass %; 0.7 mL, 1 mmol) was then added, the tube was capped, and the reaction mixture was heated in a microwave for 30 mins at 120° C. The cooled reaction mixture was poured into water and extracted twice with dichloromethane. The combined dichloromethane extracts were washed with water and brine, dried by passing through a phase-separating cartridge, then adsorbed on to silica-gel by evaporation under reduced pressure and dry-loaded onto a 24 g GOLD Rf cartridge. The mixture was then separated by chromatography (CombiFlash Rf, eluting with a dichloromethane/methanol gradient) to afford compound 1.001 (100 mg) as a white solid.

1H NMR (CDCl$_3$) δ 10.67 (br s, 1H), 4.10 (s, 3H), 3.86 (s, 3H), 3.38-3.27 (m, 1H), 2.22 (q, 2H), 1.85 (d, 2H), 1.74 (d, 1H), 1.50-1.57 (m, 2H), 1.41-1.29 (m, 3H)

Example 2: Preparation of Compound 1.017

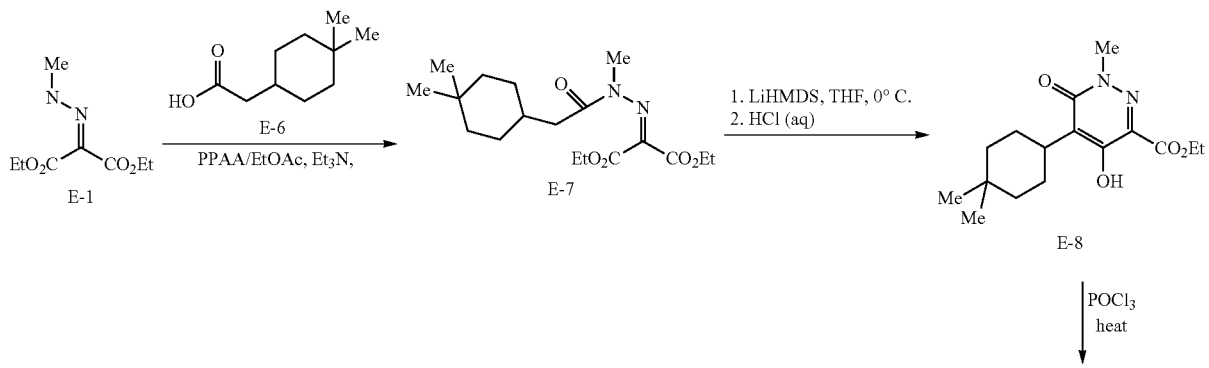

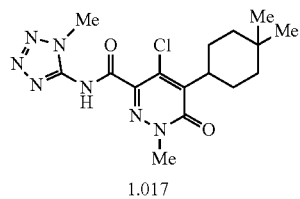 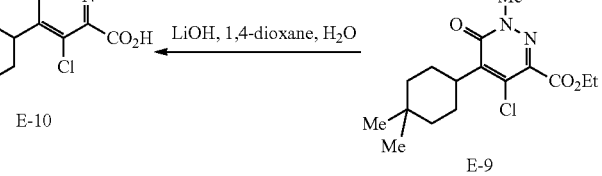

Step 1:

A solution of 1-propanephosphonic acid cyclic anhydride (PPAA) in ethyl acetate (50 mass %; 12.3 ml, 19.38 mmol) was added to a mixture of compound E-1 ((650 mg, 3.23 mmol), compound E-6 (550 mg, 3.23 mmol) and triethylamine (2.7 ml, 19.38 mmol) in a 35 ml microwave tube, and the tube was capped. The reaction mixture was heated in a microwave oven for 60 minutes at 120° C., then cooled. The cooled mixture was poured into water and extracted twice with ethyl acetate (2×50 ml). The combined ethyl acetate extracts were washed with brine solution and dried over anhydrous sodium sulfate. The solution was filtered and the solvent was removed under reduced pressure to afford the crude product, which was purified by column chromatography over silica gel, using 0% to 15% ethyl acetate/n-hexane mixtures, to afford pure compound E-7 as a pale brown oil (350 mg).

1H NMR (CDCl$_3$) δ 4.48 (q, 2H), 4.32 (q, 2H), 3.32 (s, 3H), 2.74 (d, 2H), 1.80-1.69 (m, 1H), 1.41-1.28 (m, 8H), 1.28-1.13 (m, 5H), 0.88 (s, 3H), 0.86 (s, 3H) m/z 355 (M+H)

Step 2:

Using a method analogous to that described in Example 1, Step 3, but using compound E-7 in place of compound E-2, compound E-8 was obtained as an off-white solid.

1H NMR (CDCl$_3$) δ 10.58 (s, 1H), 4.47 (q, 2H), 3.82 (s, 3H), 3.00 (m, 1H), 2.36-2.19 (m, 2H), 1.47-1.15 (m, 9H), 1.01 (s, 3H), 0.92 (s, 3H)

Step 3:

Using a method analogous to that described in Example 1, Step 4, but using compound E-8 in place of compound E-3, compound E-9 was obtained as a pale brown oil.

1H NMR (CDCl$_3$) δ 4.41 (q, 2H), 3.76 (s, 3H), 3.11 (m, 1H), 2.46-2.33 (m, 2H), 1.52-1.15 (m, 9H), 1.03 (s, 3H), 0.93 (s, 3H)

Step 4:

Using a method analogous to that described in Example 1, Step 5, but using compound E-9 in place of compound E-4, compound E-10 was obtained as an off-white solid.

1H NMR (DMSO) δ 14.05 (br, 1H), 3.64 (s, 3H), 3.04 (m, 1H), 2.40-2.24 (m, 2H), 1.47-1.38 (m, 2H), 1.33-1.17 (m, 4H), 0.99 (s, 3H), 0.92 (s, 3H)

Step 5:

Using a method analogous to that described in Example 1, Step 6, but using compound E-10 in place of compound E-5, compound 1.017 was obtained as an off-white solid.

1H NMR (CDCl$_3$) δ 10.35 (s, 1H), 4.09 (s, 3H), 3.86 (s, 3H), 3.22 (m, 1H), 2.49-2.36 (m, 2H), 1.51-1.44 (m, 2H), 1.38-1.21 (m, 4H), 1.04 (s, 3H), 0.94 (s, 3H)

TABLE 1

Examples of herbicidal compounds of the present invention.

| Compound | Chemical Structure | NMR |
|---|---|---|
| 1.001 | (structure) | 1H NMR (CDCl$_3$) δ 10.67 (br s, 1H), 4.10 (s, 3H), 3.86 (s, 3H), 3.38-3.27 (m, 1H), 2.22 (q, 2H), 1.85 (d, 2H), 1.74 (d, 1H), 1.50-1.57 (m, 2H), 1.41-1.29 (m, 3H) |
| 1.002 | (structure) | 1H NMR (CDCl3): 10.70 (s, 1H), 4.42 (q, 2H), 3.84 (s, 3H), 3.30 (m, 1H), 2.28-2.14 (m, 2H), 1.87-1.80 (m, 2H), 1.75-1.69 (m, 1H), 1.61 (t, 3H), 1.60-1.48 (m, 2H), 1.41-1.29 (m, 3H) |

TABLE 1-continued

Examples of herbicidal compounds of the present invention.

| Compound | Chemical Structure | NMR |
|---|---|---|
| 1.003 | 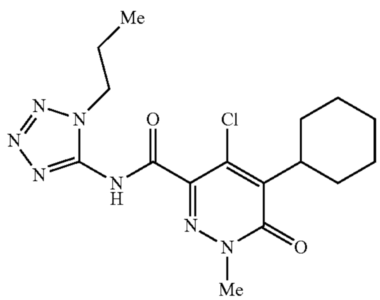 [SMILES: CCCn1nnnc1NC(=O)c1nn(C)c(=O)c(C2CCCCC2)c1Cl] | 1H NMR (CDCl3): 10.65 (s, 1H), 4.35 (q, 2H), 3.30 (m, 1H), 2.27-2.16 (m, 2H), 2.00 (m, 2H), 1.89-1.79 (m, 2H), 1.76-1.67 (m, 1H), 1.61-1.47 (m, 2H), 1.40-1.26 (m, 3H), 0.97 (t, 3H) |
| 1.004 | 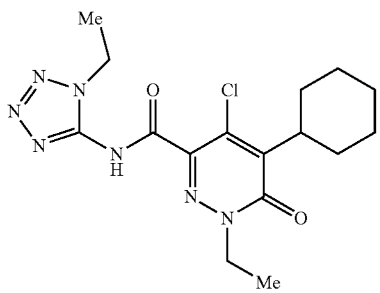 [SMILES: CCn1nnnc1NC(=O)c1nn(CC)c(=O)c(C2CCCCC2)c1Cl] | |
| 1.005 | 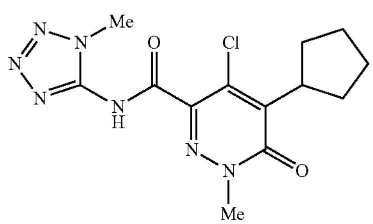 [SMILES: Cn1nnnc1NC(=O)c1nn(C)c(=O)c(C2CCCC2)c1Cl] | 1H NMR (CDCl3): 10.57 (br s, 1H), 4.08 (s, 3H), 3.86 (s, 3H), 3.69 (m, 1H), 2.10-1.90 (m, 4H), 1.82-1.62 (m, 4H) |
| 1.006 | 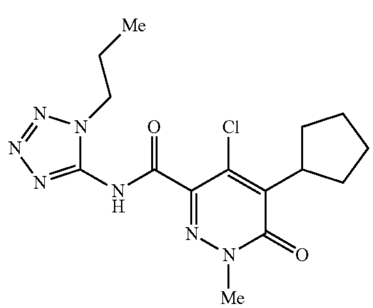 [SMILES: CCCn1nnnc1NC(=O)c1nn(C)c(=O)c(C2CCCC2)c1Cl] | 1H NMR (CDCl3): 10.33 (br s, 1H), 4.36 (t, 2H), 3.85 (s, 3H), 3.67 (m, 1H), 2.13-1.88 (m, 6H), 1.83-1.61 (m, 4H), 0.97 (t, 3H) |
| 1.007 | 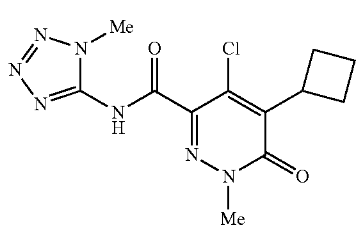 [SMILES: Cn1nnnc1NC(=O)c1nn(C)c(=O)c(C2CCC2)c1Cl] | |

TABLE 1-continued

Examples of herbicidal compounds of the present invention.

| Compound | Chemical Structure | NMR |
|---|---|---|
| 1.008 | 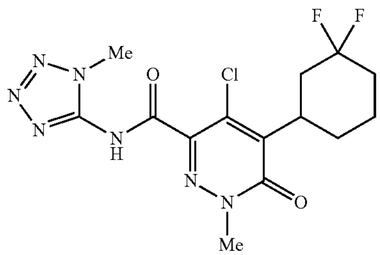 [SMILES: Cn1nnnc1NC(=O)c1nn(C)c(=O)c(C2CCCC(F)(F)C2)c1Cl] | |
| 1.009 | 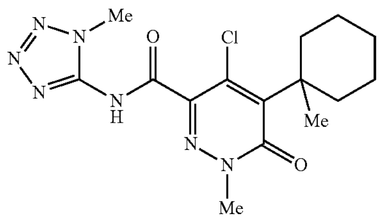 [SMILES: Cn1nnnc1NC(=O)c1nn(C)c(=O)c(C2(C)CCCCC2)c1Cl] | |
| 1.010 | 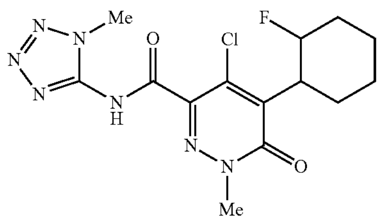 [SMILES: Cn1nnnc1NC(=O)c1nn(C)c(=O)c(C2CCCCC2F)c1Cl] | |
| 1.011 | 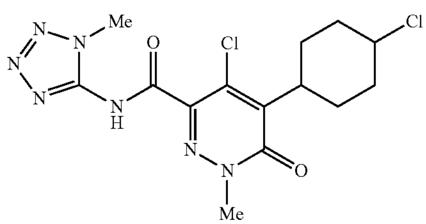 [SMILES: Cn1nnnc1NC(=O)c1nn(C)c(=O)c(C2CCC(Cl)CC2)c1Cl] | |
| 1.012 | 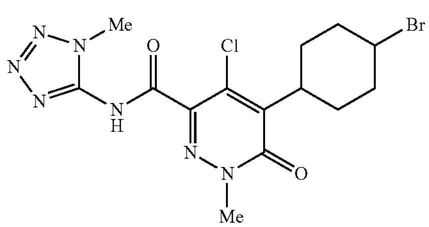 [SMILES: Cn1nnnc1NC(=O)c1nn(C)c(=O)c(C2CCC(Br)CC2)c1Cl] | |
| 1.013 | 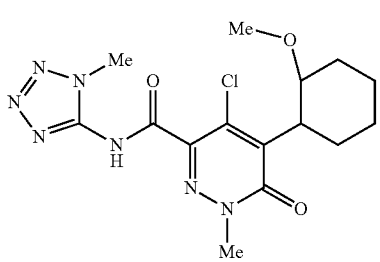 [SMILES: COC1CCCCC1c1c(Cl)c(C(=O)Nc2nnnn2C)nn(C)c1=O] | |

TABLE 1-continued

Examples of herbicidal compounds of the present invention.

| Compound | Chemical Structure | NMR |
|---|---|---|
| 1.014 | 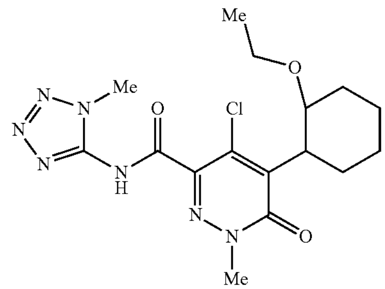 [SMILES: CCOC1CCCCC1c1c(Cl)c(C(=O)Nc2nnnn2C)nn(C)c1=O] | |
| 1.015 | 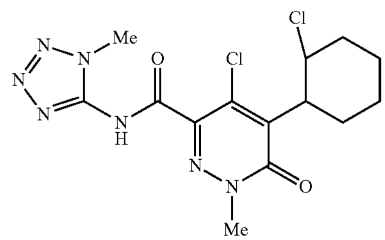 [SMILES: Cn1nnnc1NC(=O)c1nn(C)c(=O)c(C2CCCCC2Cl)c1Cl] | |
| 1.016 | 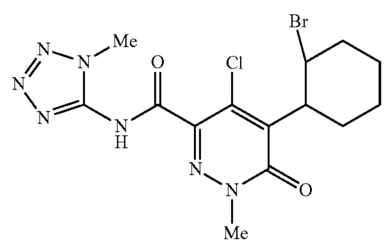 [SMILES: Cn1nnnc1NC(=O)c1nn(C)c(=O)c(C2CCCCC2Br)c1Cl] | |
| 1.017 | 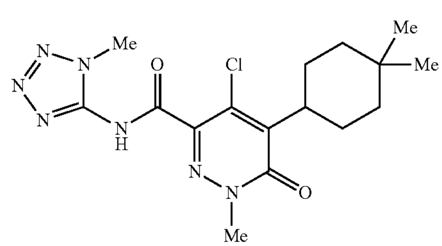 [SMILES: Cn1nnnc1NC(=O)c1nn(C)c(=O)c(C2CCC(C)(C)CC2)c1Cl] | 1H NMR (CDCl3): 10.35 (s, 1H), 4.09 (s, 3H), 3.86 (s, 3H), 3.22 (m, 1H), 2.49-2.36 (m, 2H), 1.51-1.44 (m, 2H), 1.38-1.21 (m, 4H), 1.04 (s, 3H), 0.94 (s, 3H) |
| 1.018 | 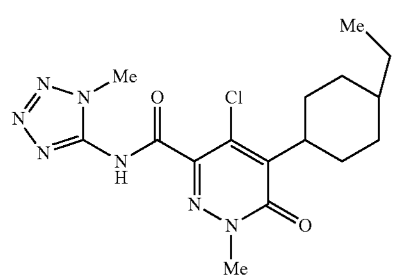 [SMILES: CCC1CCC(c2c(Cl)c(C(=O)Nc3nnnn3C)nn(C)c2=O)CC1] | |

TABLE 1-continued

Examples of herbicidal compounds of the present invention.

| Compound | Chemical Structure | NMR |
|---|---|---|
| 1.019 | 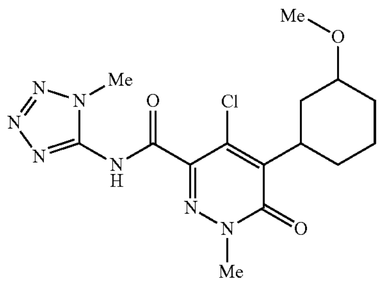 [SMILES: COC1CCCC(c2c(Cl)c(C(=O)Nc3nnnn3C)nn(C)c2=O)C1] | |
| 1.020 | 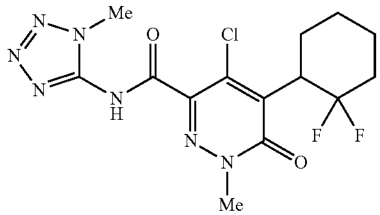 [SMILES: Cn1nnnc1NC(=O)c1nn(C)c(=O)c(C2CCCCC2(F)F)c1Cl] | |
| 1.021 | 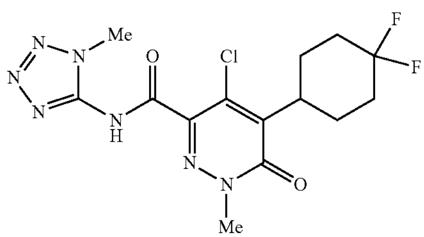 [SMILES: Cn1nnnc1NC(=O)c1nn(C)c(=O)c(C2CCC(F)(F)CC2)c1Cl] | |
| 1.022 | 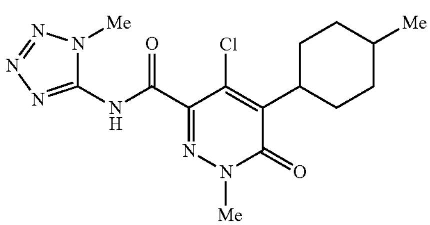 [SMILES: CC1CCC(c2c(Cl)c(C(=O)Nc3nnnn3C)nn(C)c2=O)CC1] | 1H NMR CDCl3): 10.52 (s, 1H), 4.08 (s, 3H), 3.85 (s, 3H), 3.24 (m, 1H), 2.31-2.19 (m, 2H), 1.84-1.75 (m, 2H), 1.64-1.51 (m, 3H), 1.09-0.97 (m, 2H), 0.91 (d, 3H) |
| 1.023 | 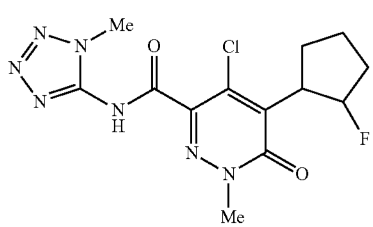 [SMILES: Cn1nnnc1NC(=O)c1nn(C)c(=O)c(C2CCCC2F)c1Cl] | |
| 1.024 | 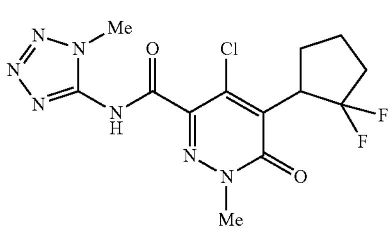 [SMILES: Cn1nnnc1NC(=O)c1nn(C)c(=O)c(C2CCCC2(F)F)c1Cl] | |

TABLE 1-continued

Examples of herbicidal compounds of the present invention.

| Compound | Chemical Structure | NMR |
|---|---|---|
| 1.025 | 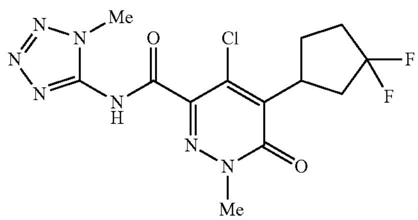 [SMILES: Cn1nnnc1NC(=O)c1nn(C)c(=O)c(C2CCC(F)(F)C2)c1Cl] | |
| 1.026 | 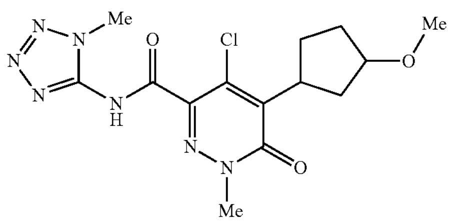 [SMILES: COC1CCC(c2c(Cl)c(C(=O)Nc3nnnn3C)nn(C)c2=O)C1] | |
| 1.027 | 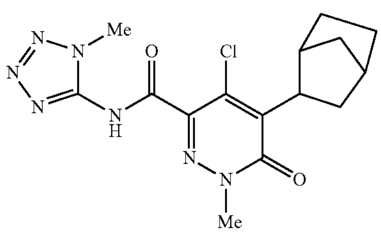 [SMILES: Cn1nnnc1NC(=O)c1nn(C)c(=O)c(C2CC3CCC2C3)c1Cl] | |
| 1.028 | 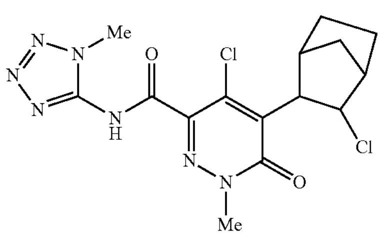 [SMILES: Cn1nnnc1NC(=O)c1nn(C)c(=O)c(C2C3CCC(C3)C2Cl)c1Cl] | |
| 1.029 | 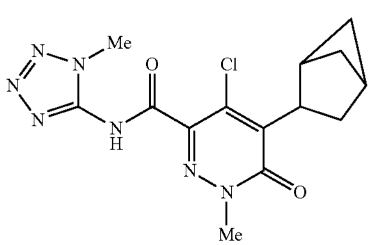 [SMILES: Cn1nnnc1NC(=O)c1nn(C)c(=O)c(C2CC3CC2C3)c1Cl] | |
| 1.030 | 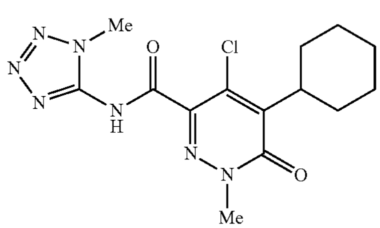 [SMILES: Cn1nnnc1NC(=O)c1nn(C)c(=O)c(C2CCCCC2)c1Cl] | 1H NMR CDCl3): 9.50 (br, 1H), 7.79 (s, 1H), 3.86 (s, 3H), 3.76 (s, 3H), 3.29 (m, 1H), 2.27-2.11 (m, 2H), 1.87-1.76 (m, 2H), 1.75-1.68 (m, 1H), 1.57-1.47 (m, 2H), 1.38-1.25 (m, 3H) |

TABLE 1-continued

Examples of herbicidal compounds of the present invention.

| Compound | Chemical Structure | NMR |
| --- | --- | --- |
| 1.031 | 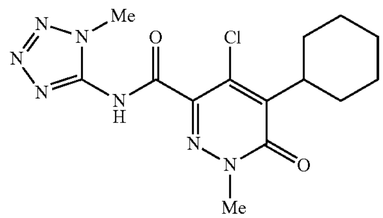 [SMILES: Cn1nnnc1NC(=O)c1nn(C)c(=O)c(C2CCCCC2)c1Cl] | 1H NMR (CDCl3): 12.42 (br, 1H), 7.77 (s, 1H), 3.74 (s, 3H), 3.63 (s, 3H), 3.23 (m, 1H), 2.29-2.14 (m, 2H), 1.87-1.78 (m, 2H), 1.72-1.67 (m, 1H), 1.60-1.48 (m, 2H), 1.49-1.26 (m, 3H) |
| 1.032 | 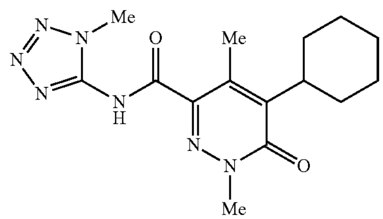 [SMILES: Cc1c(C(=O)Nc2nnnn2C)nn(C)c(=O)c1C1CCCCC1] | |
| 1.033 | 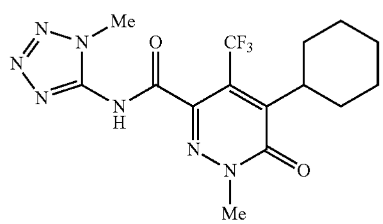 | |
| 1.034 | 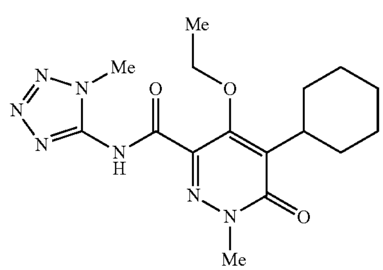 [SMILES: CCOc1c(C(=O)Nc2nnnn2C)nn(C)c(=O)c1C1CCCCC1] | |
| 1.035 | 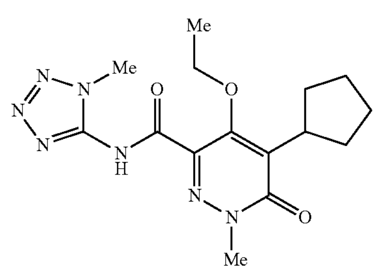 [SMILES: CCOc1c(C(=O)Nc2nnnn2C)nn(C)c(=O)c1C1CCCC1] | |

BIOLOGICAL EXAMPLES (i) Comparative Testing

Seeds of a variety of test species are sown in standard soil in pots. After cultivation for one day under controlled conditions in a glasshouse (at 24/16° C., day/night; 14 hours light; 65% humidity), an aqueous spray solution derived from the formulation of the technical active ingredient in 0.6 ml acetone and 45 ml formulation solution containing 10.6% Emulsogen EL (Registry number 61791-12-6), 42.2% N-methyl pyrrolidone, 42.2% dipropylene glycol monomethyl ether (CAS RN 34590-94-8) and 0.2% X-77 (CAS RN 11097-66-8) is applied.

The test plants are then grown in a glasshouse under controlled conditions in a glasshouse (at 24/16° C., day/night; 14 hours light; 65% humidity) and watered twice daily. After 21 days, the test is evaluated (100=total damage to plant; 0=no damage to plant). Test plants (weed species) include: *Alopecurus myosuroides* (ALOMY), *Bidens pilosa* (BIDPI), *Euphorbia heterophylla* (EPHHL), *Lolium perenne* (LOLPE), *Panicum milaceum* (PANMI), *Sida spinosa* (SIDSP) and *Stellaria media* STEME).

| Compound | Rate | ALOMY | BIDPI | EPHHL | LOLPE | PANMI | SIDSP | STEME |
|---|---|---|---|---|---|---|---|---|
| 1.001 | 125 | 40 | 100 | 90 | 60 | 80 | 90 | 100 |
| A | 125 | 0 | 0 | 0 | 10 | 0 | 0 | 50 |
| 1.001 | 250 | 40 | 100 | 90 | 60 | 80 | 90 | 100 |
| A | 250 | 20 | 40 | 20 | 20 | 0 | 0 | 60 |

Compound A = 2-(4-chloro-5-cyclohexyl-1-methyl-6-oxo-pyridazine-3-carbonyl)cyclohexane-1,3-dione = Compound 22 referred to in WO2014/031971.

This test shows that the compounds of the present invention provide surprisingly superior weed control against numerous weed species when compared to the pyridazinone compounds disclosed in WO2014/031971.

(ii) Further Testing

Seeds of a variety of test species are sown in standard soil in pots (*Lolium perenne* (LOLPE), *Solanum nigrum* (SOLNI), *Amaranthus retoflexus* (AMARE), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/h unless otherwise stated. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

| | POST Application | | | | | | PRE Application | | | | | |
|---|---|---|---|---|---|---|---|---|---|---|---|---|
| CMP | LOLPE | SOLNI | AMARE | SETFA | ECHCG | IPOHE | LOLPE | SOLNI | AMARE | SETFA | ECHCG | IPOHE |
| 1.001 | 5 | 5 | 5 | 5 | 5 | 5 | 5 | 5 | 5 | 5 | 5 | 5 |
| 1.002 | 5 | 5 | 5 | 5 | 5 | 5 | 5 | 5 | 5 | 5 | 5 | 5 |
| 1.003 | 4 | 5 | 5 | 5 | 5 | 5 | 5 | 5 | 5 | 5 | 5 | 5 |
| 1.005 | 5 | 5 | 5 | 5 | 5 | 5 | 5 | 5 | 5 | 5 | 5 | 5 |
| 1.006 | 5 | 5 | 5 | 5 | 5 | 5 | 5 | 5 | 5 | 5 | 5 | 4 |
| 1.017 | 5 | 5 | 5 | 5 | 5 | 5 | 5 | 5 | 5 | 5 | 5 | 4 |
| 1.022 | 5 | 5 | 5 | 5 | 5 | 5 | 5 | 5 | 5 | 5 | 5 | 5 |
| 1.030 | 5 | 5 | 5 | 5 | 5 | 4 | 5 | 5 | 5 | 5 | 5 | 2 |
| 1.031 | 4 | 5 | 5 | 5 | 4 | 4 | 3 | 5 | 5 | 4 | 5 | 4 |

The invention claimed is:

1. A compound of Formula (I):

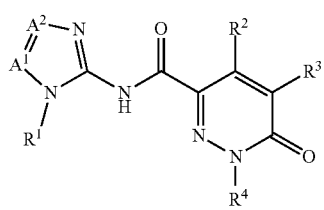

(I)

or an agronomically acceptable salt thereof, wherein:

$A^1$ and $A^2$ are independently selected from CH and N, wherein $A^1$ and $A^2$ are not both CH;

$R^1$ is selected from the group consisting of $C_1$-$C_6$alkyl-, $C_1$-$C_6$haloalkyl- and $C_1$-$C_6$alkoxy-$C_1$-$C_3$alkyl-;

$R^2$ is selected from the group consisting of $C_1$-$C_6$alkyl-, $C_1$-$C_6$haloalkyl-, halogen and —O—$R^5$;

$R^3$ is $C_3$-$C_8$cycloalkyl- which is optionally substituted by one or more substituents selected from the group consisting of halogen, $C_1$-$C_6$alkyl-, $C_1$-$C_6$alkoxy- and $C_1$-$C_6$haloalkyl-;

$R^4$ is selected from the group consisting of $C_1$-$C_6$alkyl-, $C_3$-$C_6$-cycloalkyl- and $C_1$-$C_6$ haloalkyl-; and $R^5$ is selected from the group consisting of $C_1$-$C_6$alkyl-, $C_1$-$C_6$haloalkyl-, $C_1$-$C_6$alkoxy-$C_1$-$C_3$alkyl-.

2. The compound according to claim 1, wherein $A^1$ and $A^2$ are N.

3. The compound of claim 1, wherein $R^1$ is selected from the group consisting of methyl, ethyl and n-propyl.

4. The compound according to claim 1, wherein $R^2$ is chloro.

5. The compound according to claim 1, wherein $R^3$ is a $C_3$-$C_8$cycloalkyl- selected from the group consisting of cyclobutyl, cyclopentyl, cyclohexyl, bicyclo[2.1.1]hexane and bicyclo[2.2.1]heptane, wherein said $C_3$-$C_8$cycloalkyl- is optionally substituted by one or more substituents selected from the group consisting of halogen, $C_1$-$C_6$alkyl-, $C_1$-$C_6$alkoxy- and $C_1$-$C_6$haloalkyl-.

6. The compound according to claim 5, wherein $R^3$ is cyclopentyl or cyclohexyl.

7. The compound according to claim 1, wherein $R^4$ is methyl.

8. A herbicidal composition comprising the compound according to claim 1 and an agriculturally acceptable formulation adjuvant.

9. The herbicidal composition according to claim 8, further comprising at least one additional pesticide.

10. The herbicidal composition according to claim 9, wherein the additional pesticide is a herbicide or herbicide safener.

11. A method of controlling weeds at a locus comprising application to the locus of a weed controlling amount of the compound according to claim 1.

* * * * *